United States Patent
Chirayil et al.

(10) Patent No.: US 11,267,832 B2
(45) Date of Patent: Mar. 8, 2022

(54) MN(II)-BASED SENSORS TO DETECT ZINC IN VIVO WITH MRI

(71) Applicant: The Board of Regents of the University of Texas System, Austin, TX (US)

(72) Inventors: Sara Chirayil, Plano, TX (US); Veronica Clavijo Jordan, Dallas, TX (US); Andre F. Martins, Plano, TX (US); A. Dean Sherry, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 16/658,471

(22) Filed: Oct. 21, 2019

(65) Prior Publication Data
US 2020/0123183 A1    Apr. 23, 2020

Related U.S. Application Data

(60) Provisional application No. 62/748,887, filed on Oct. 22, 2018.

(51) Int. Cl.
| | | |
|---|---|---|
| C07F 13/00 | (2006.01) | |
| A61K 9/00 | (2006.01) | |
| A61K 49/10 | (2006.01) | |
| C07D 213/82 | (2006.01) | |

(52) U.S. Cl.
CPC ............ *C07F 13/00* (2013.01); *A61K 9/0019* (2013.01); *A61K 49/106* (2013.01); *C07D 213/82* (2013.01)

(58) Field of Classification Search
CPC ............ A61K 49/00; A61K 9/00; C07F 13/00
See application file for complete search history.

(56) References Cited

U.S. PATENT DOCUMENTS

| | | | |
|---|---|---|---|
| 2011/0009605 A1* | 1/2011 | De Leon-Rodriguez | .................... C07F 5/003 534/10 |
| 2017/0106103 A1* | 4/2017 | Preihs | .................... A61B 5/055 |

FOREIGN PATENT DOCUMENTS

| | | |
|---|---|---|
| WO | WO 2011/156728 | 12/2011 |
| WO | WO 2017/027834 | 2/2017 |

OTHER PUBLICATIONS

Eric M. Gale et al., A Manganese Alternative to Gadolinium for MRI Contrast, JACS, 137(49), 15548-15557. (Year: 2015).*
Caravan et al., "Gadolinium(III) Chelates as MRI Contrast Agents: Structure, Dynamics, and Applications," *Chemical Reviews*, 99:2293-2352, 1999.
Chirayil et al., "A manganese(II)-based responsive contrast agent detects glucose-stimulated zinc secretion from the mouse pancreas and prostate by MRI," *ChemRxiv*, and Supplementary Materials, 2020.
Clavijo Jordan et al., "Imaging glucose-stimulated zinc secretion from the prostate and pancreas using a Mn(II)-based zinc sensor," Abstract 3076, International Society of Magnetic Resonance in Medicine, 2018.
Esqueda et al., "A new gadolinium-based MRI zinc sensor," *J. Am. Chem. Soc.*, 131(32): 11387-11391, 2009.
Gale et al., "A Manganese Alternative to Gadolinium for MRI Contrast," *J. Am. Chem. Soc.*, 137:15548-15557, 2015.
Huang et al., "Chlorotoxin-modified macromolecular contrast agent for MRI tumor diagnosis," *Biomaterials*, 32:5177-5186, 2011.
Lin and Koretsky, "Manganese ion enhances $T_1$-weighted MRI during brain activation: an approach to direct imaging of brain function," *Magn Reson Med.*, 38(3):378-388, 1997.
Shiraishi et al., "Polyion complex micelle MRI contrast agents from poly(ethylene glycol)-b-poly(l-lysine) block copolymers having Gd-DOTA; preparations and their control of T(1)-relaxivities and blood circulation characteristics," *Journal of Controlled Release*, 148:160-167, 2010.

* cited by examiner

*Primary Examiner* — Michael G. Hartley
*Assistant Examiner* — Jagadishwar R Samala
(74) *Attorney, Agent, or Firm* — Parker Highlander PLLC

(57) ABSTRACT

In some aspects, the present disclosure provides compounds of the formula:

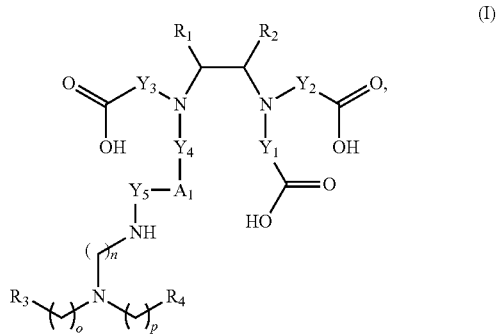

wherein the variables are defined herein. In some aspects, the present disclosure provides methods of preparing imaging agents, compositions thereof, and methods of imaging using said imaging agents or compositions thereof.

18 Claims, 3 Drawing Sheets

MN(II)-BASED SENSORS TO DETECT ZINC IN VIVO WITH MRI

PRIORITY CLAIM

This application claims benefit of priority to U.S. Provisional Application Ser. No. 62/748,887, filed Oct. 22, 2018, the entire contents of which are hereby incorporated by reference.

GOVERNMENT SUPPORT CLAUSE

This invention was made with government support under Grant Nos. P41-EB015908 and RO1-DK095416 awarded by the National Institutes of Health. The government has certain rights in the invention.

BACKGROUND

1. Field

The present disclosure relates generally to the fields of diagnostic testing and imaging agents. The disclosure provides, for example, novel ligands for the preparation of MRI imaging agents, novel MRI imaging agents, compositions of the novel imaging agents, and methods of use thereof.

2. Description of Related Art

Molecular imaging is used for visualizing biological targets and to understand their complexities for diagnosis and treatment purposes. Through an accurate and real-time imaging of biological targets, a thorough understanding of the fundamental biological processes can be gained leading to the successful diagnose of various diseases (Weissleder, 2006). In particular, MRI imaging can be useful to help visualize those biological processes. Gadolinium is a known and well characterized $T_1$ contrast agent with useful and important physical properties for use in MRI imaging agents. Unfortunately, this ion is highly toxic in a "free" state, and hence it is typically used as a thermodynamically stable and kinetically inert complex.

Zinc(II) ions in particular are of particular interest as zinc is the second most abundant trace element in mammalian tissues and plays an extensive role in controlling gene transcription and metalloenzyme function (Esqueda, et al., 2009). The prostate, pancreas, and brain are known to contain relatively large amounts of zinc ions relative to other issues in the body. Zinc and the movement of zinc ions has been associated with the formation of β-amyloids, the release of insulin by β-cells in the pancreas and changes in concentration in zinc is associated with formation of tumors particular in prostate tissue. As such, a method of in vivo imaging of zinc represents a key goal to helping understand these biological functions and associated disease states such as Alzheimer's disease, diabetes, and cancer.

Safety concerns associated with gadolinium deposition and onset of nephrogenic systemic fibrosis after repeated usage of some gadolinium-based MRI contract agents are on the rise. As such, alternative contrast agents are needed.

SUMMARY

In some aspects, the present disclosure provides compounds of the formula:

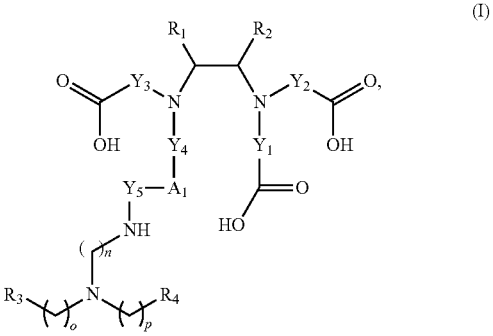

wherein:
n is 1, 2, 3, 4, 5, or 6;
o and p are each independently 1, 2, or 3;
$A_1$ is heteroarenediyl$_{(C \leq 12)}$ or substituted heteroarenediyl$_{(C \leq 12)}$;
$R_1$ and $R_2$ are each independently hydrogen; or
  alkyl$_{(C \leq 12)}$, aryl$_{(C \leq 12)}$, heteroaryl$_{(C \leq 12)}$, or a substituted version of any of these groups; or
$R_1$ and $R_2$ are taken together and are alkanediyl$_{(C \leq 12)}$, substituted alkanediyl$_{(C \leq 12)}$, alkenediyl$_{(C \leq 12)}$, or substituted alkenediyl$_{(C \leq 12)}$;
$R_3$ and $R_4$ are each independently heteroaryl$_{(C \leq 12)}$ or substituted heteroaryl$_{(C \leq 12)}$;
$Y_1$, $Y_2$, $Y_3$, and $Y_4$ are each independently alkanediyl$_{(C \leq 4)}$ or substituted alkanediyl$_{(C \leq 4)}$; and
$Y_5$ is a covalent bond or —C(O)—; or
  alkanediyl$_{(C \leq 12)}$, substituted alkanediyl$_{(C \leq 12)}$, -alkanediyl$_{(C \leq 12)}$-C(O)—, or substituted -alkanediyl$_{(C \leq 12)}$-C(O)—;
or a metal complex, a deprotonated form, a hydrate, or a salt thereof.

In some embodiments, the compounds are further defined as:

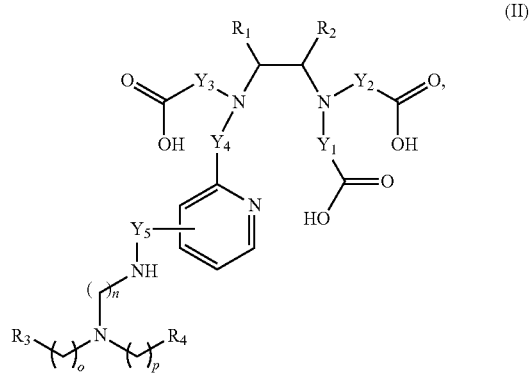

wherein:
n is 1, 2, 3, 4, 5, or 6;
o and p are each independently 1, 2, or 3;
$R_1$ and $R_2$ are each independently hydrogen; or
  alkyl$_{(C \leq 12)}$, aryl$_{(C \leq 12)}$, heteroaryl$_{(C \leq 12)}$, or a substituted version of any of these groups; or R₁ and R₂ are taken together and are alkanediyl$_{(C≤12)}$, substituted alkanediyl$_{(C≤12)}$, alkenediyl$_{(C≤12)}$, or substituted alkenediyl$_{(C≤12)}$;

R₃ and R₄ are each independently heteroaryl$_{(C≤12)}$ or substituted heteroaryl$_{(C≤12)}$;

Y₁, Y₂, Y₃, and Y₄ are each independently alkanediyl$_{(C≤4)}$ or substituted alkanediyl$_{(C≤4)}$; and Y₅ is a covalent bond or —C(O)—; or alkanediyl$_{(C≤12)}$, substituted alkanediyl$_{(C≤12)}$, -alkanediyl$_{(C≤12)}$-C(O)—, or substituted -alkanediyl$_{(C≤12)}$-C(O)—;

or a metal complex, a deprotonated form, a hydrate, or a salt thereof.

In some embodiments, the compounds are further defined as:

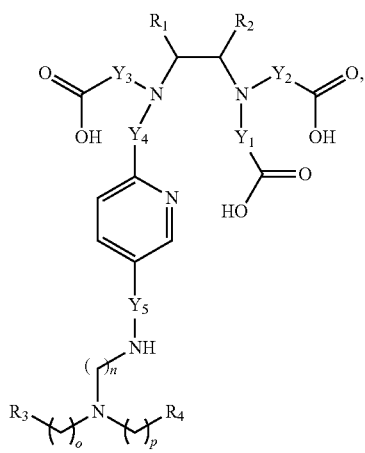

(III)

wherein:
n is 1, 2, 3, 4, 5, or 6;
o and p are each independently 1, 2, or 3;
R₁ and R₂ are each independently hydrogen; or
  alkyl$_{(C≤12)}$, aryl$_{(C≤12)}$, heteroaryl$_{(C≤12)}$, or a substituted version of any of these groups; or
R₁ and R₂ are taken together and are alkanediyl$_{(C≤12)}$, substituted alkanediyl$_{(C≤12)}$, alkenediyl$_{(C≤12)}$, or substituted alkenediyl$_{(C≤12)}$;
R₃ and R₄ are each independently heteroaryl$_{(C≤12)}$ or substituted heteroaryl$_{(C≤12)}$;
Y₁, Y₂, Y₃, and Y₄ are each independently alkanediyl$_{(C≤4)}$ or substituted alkanediyl$_{(C≤4)}$; and
Y₅ is a covalent bond or —C(O)—; or
  alkanediyl$_{(C≤12)}$, substituted alkanediyl$_{(C≤12)}$, -alkanediyl$_{(C≤12)}$-C(O)—, or substituted -alkanediyl$_{(C≤12)}$-C(O)—;

or a metal complex, a deprotonated form, a hydrate, or a salt thereof.

In some embodiments, the compounds are further defined as:

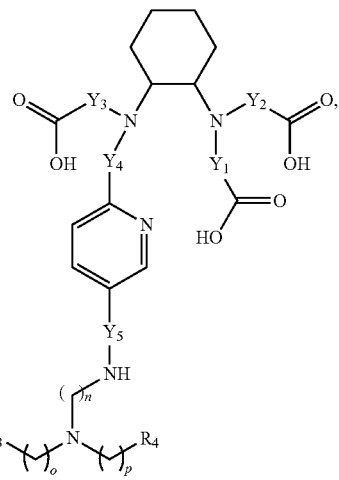

(IV)

wherein:
n is 1, 2, 3, 4, 5, or 6;
o and p are each independently 1, 2, or 3;
R₃ and R₄ are each independently heteroaryl$_{(C≤12)}$ or substituted heteroaryl$_{(C≤12)}$;
Y₁, Y₂, Y₃, and Y₄ are each independently alkanediyl$_{(C≤4)}$ or substituted alkanediyl$_{(C≤4)}$; and
Y₅ is a covalent bond or —C(O)—; or
  alkanediyl$_{(C≤12)}$, substituted alkanediyl$_{(C≤12)}$, -alkanediyl$_{(C≤12)}$-C(O)—, or
  substituted -alkanediyl$_{(C≤12)}$-C(O)—;

or a metal complex, a deprotonated form, a hydrate, or a salt thereof.

In some embodiments, the compounds are further defined as:

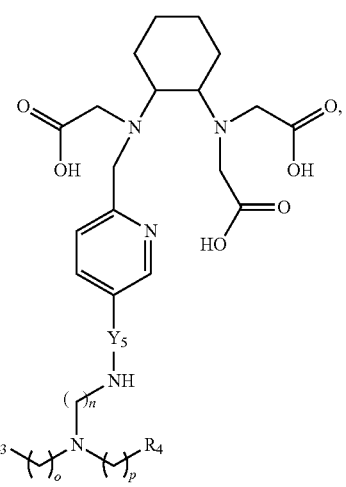

(V)

wherein:
n is 1, 2, 3, 4, 5, or 6;
o and p are each independently 1, 2, or 3;
R₃ and R₄ are each independently heteroaryl$_{(C≤12)}$ or substituted heteroaryl$_{(C≤12)}$;
Y₅ is a covalent bond or —C(O)—; or alkanediyl$_{(C≤12)}$, substituted alkanediyl$_{(C≤12)}$, -alkanediyl$_{(C≤12)}$-C(O)—, or substituted -alkanediyl$_{(C≤12)}$-C(O)—;

or a metal complex, a deprotonated form, a hydrate, or a salt thereof.

In some embodiments, $R_3$ is heteroaryl$_{(C≤12)}$, such as pyridin-2-yl. In some embodiments, $R_4$ is heteroaryl$_{(C≤12)}$, such as pyridin-2-yl. In some embodiments, n is 2. In some embodiments, o is 1 or 2. In some embodiments, p is 1 or 2. In some embodiments, $Y_5$ is —C(O)—.

In some embodiments, the compound is a metal complex and further comprises a metal ion chelated as defined by the formula:

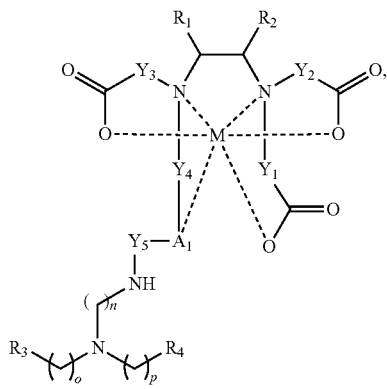

(VI)

wherein:

$A_1$, n, o, p, $R_1$, $R_2$, $R_3$, $R_4$, $Y_1$, $Y_2$, $Y_3$, $Y_4$, and $Y_5$ are as defined above; and M is a metal ion;

or a deprotonated form, a hydrate, or a salt thereof. In some embodiments, M is $Mn^{2+}$.

In some embodiments, the compound is further defined as:

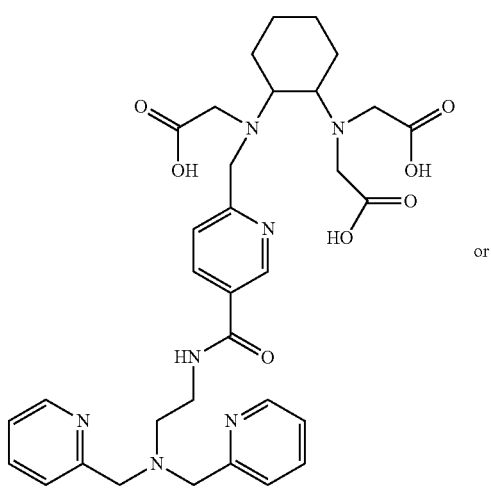

or

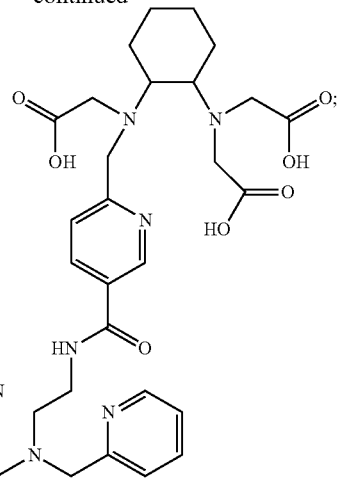

or a metal complex, a deprotonated form, a hydrate, or a salt thereof.

In some embodiments, the compound is further defined as a metal complex of the formula:

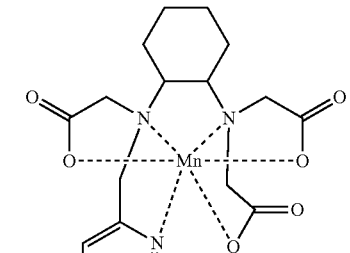

or

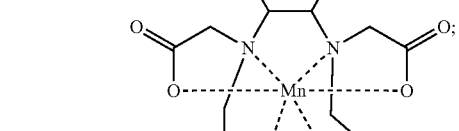

or a deprotonated form, a hydrate, or a salt thereof.

In some embodiments, the compound is further defined as a hydrate of the formula:

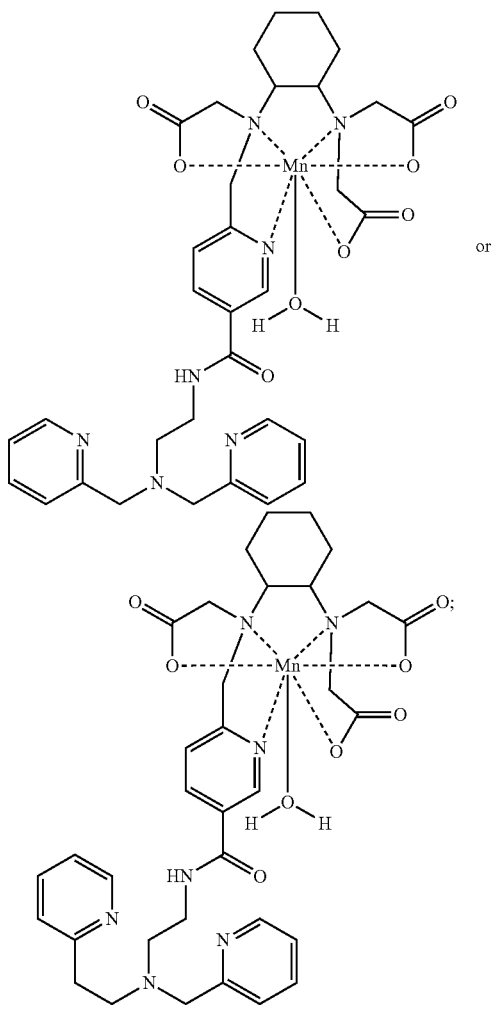

or a deprotonated form or a salt thereof.

In another aspect, the present disclosure provides pharmaceutical compositions comprising a compound of the present disclosure and a pharmaceutically acceptable carrier. In some embodiments, the pharmaceutical composition is formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. In some embodiments, the pharmaceutical composition is formulated as a unit dose form in an amount sufficient to image a patient when administered thereto.

In still another aspect, the present disclosure provides methods of imaging a patient comprising the steps of:
a) administering to the patient a compound or composition described herein; and
b) obtaining an imaging scan of the patient.

In some embodiments, the method comprises detecting the presence of $Zn^{2+}$ ions in tissue. In some embodiments, the obtained imaging scan is from an MRI. In some embodiments, the method further comprises analyzing the imaging scan. In further embodiments, analyzing the imaging scan comprises identifying changes in $Zn^{2+}$ concentration. In some embodiments, the imaging is performed in vivo. In some embodiments, analyzing the imaging scan produces a diagnosis of a disease. In further embodiments, the disease is diabetes mellitus or cancer, such as prostate cancer. In some embodiments, the patient is a mammal, such as a human. In some embodiments, the method further comprises administering human serum albumin (HSA).

In yet another aspect, the present disclosure provides methods of imaging the pancreas in vivo in a patient to determine the onset of β-cell degeneration comprising the steps of:
a) administering to the patient a compound or composition described herein;
b) obtaining an imaging scan of the patient; and
c) determining the presence of $Zn^{2+}$ ions.

In some embodiments, the imaging scan is from an MRI. In some embodiments, the method further comprises determining the concentration of $Zn^{2+}$ ions. In some embodiments, the method further comprises administering insulin to the patient before collecting the imaging scan. In some embodiments, the onset of β-cell degeneration indicates the onset of diabetes mellitus. In some embodiments, the patient is a human.

In still another aspect, the present disclosure provides methods of imaging the prostate in vivo in a patient to determine the presence of a prostate tumor comprising the steps of:
a) administering to the patient a compound or composition described herein;
b) obtaining an imaging scan of the patient; and
c) determining the presence of $Zn^{2+}$ ions.

In some embodiments, the imaging scan is from an MRI. In some embodiments, the method further comprises determining the concentration of $Zn^{2+}$ ions. In some embodiments, lower concentration of $Zn^{2+}$ ions indicates the presence of a prostate tumor. In some embodiments, the prostate tumor is a malignant prostate tumor. In some embodiments, the patient is a human.

In yet another aspect, the present disclosure provides methods of preparing an imaging agent comprising contacting a ligand of the formula:

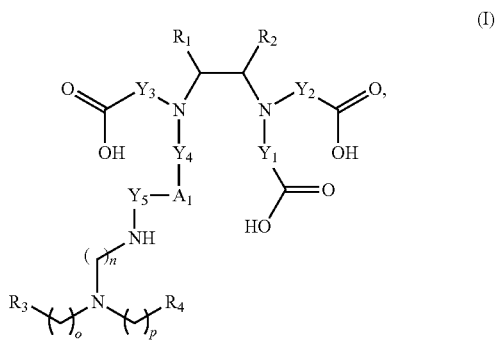

wherein:
n is 1, 2, 3, 4, 5, or 6;

o and p are each independently 1, 2, or 3;

$A_1$ is heteroarenediyl$_{(C \leq 12)}$ or substituted heteroarenediyl$_{(C \leq 12)}$;

$R_1$ and $R_2$ are each independently hydrogen; or alkyl$_{(C \leq 12)}$, aryl$_{(C \leq 12)}$, heteroaryl$_{(C \leq 12)}$, or a substituted version of any of these groups; or $R_1$ and $R_2$ are taken together and are alkanediyl$_{(C \leq 12)}$, substituted alkanediyl$_{(C \leq 12)}$, alkenediyl$_{(C \leq 12)}$, or substituted alkenediyl$_{(C \leq 12)}$;

$R_3$ and $R_4$ are each independently heteroaryl$_{(C \leq 12)}$ substituted heteroaryl$_{(C \leq 12)}$;

$Y_1, Y_2, Y_3$, and $Y_4$ are each independently alkanediyl$_{(C \leq 4)}$ or substituted alkanediyl$_{(C \leq 4)}$; and $Y_5$ is a covalent bond or —C(O)—; or alkanediyl$_{(C \leq 12)}$, substituted alkanediyl$_{(C \leq 12)}$, -alkanediyl$_{(C \leq 12)}$-C(O)—, or substituted -alkanediyl$_{(C \leq 12)}$-C(O)—;

with a metal salt to form a compound of the formula:

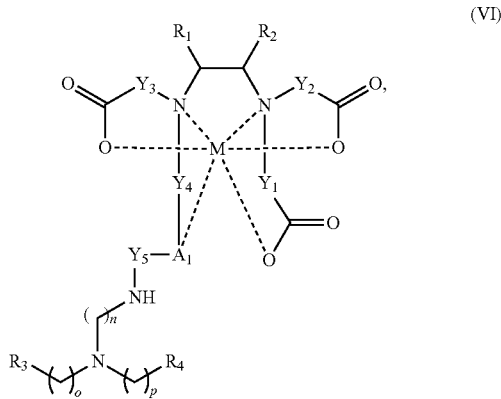

(VI)

wherein:

$A_1$, n, o, p, $R_1, R_2, R_3, R_4, Y_1, Y_2, Y_3, Y_4$, and $Y_5$ are as defined above; and M is a metal ion;

or a deprotonated form, a hydrate, or a salt thereof.

In some embodiments, the method further comprises a solvent, such as water. In some embodiments, the method further comprises an acid or a base. In some embodiments, method comprises an acid, such as hydrochloric acid. In some embodiments, the method comprises a base, such as sodium hydroxide. In some embodiments, the metal salt is a manganese salt, such as MnCl$_2$.

Other objects, features, and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DESCRIPTION OF ILLUSTRATIVE EMBODIMENTS

Figure 1:
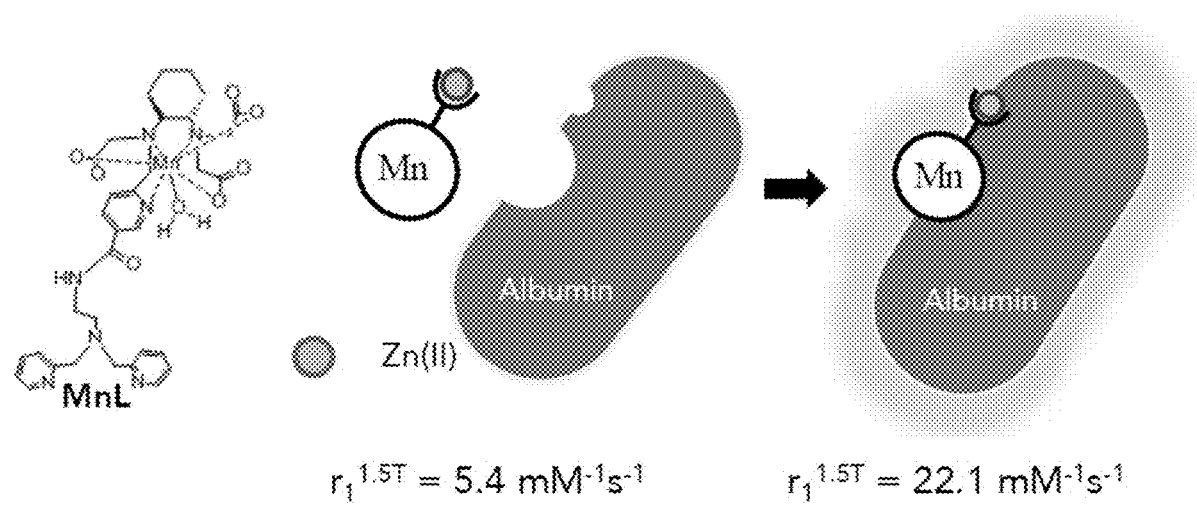
FIG. 1 shows the zinc detection mechanism with Mn-based contrast agent. Compound 5 in its "off" configuration has a longitudinal relaxivity of $r_1^{1.5T}$=3.5 mM$^{-1}$s$^{-1}$ and once in its "on" configuration bound to Zn(II) and HSA relaxivity increases to $r_1^{1.5T}$=14.1 mM$^{-1}$s$^{-1}$.

In some aspects, the present disclosure provides contrast agents containing a central manganese(II) 1,2-diamine moiety and a zinc(II) binding unit, namely di-2-picolylamine, that are linked to the manganese moiety. Upon complexation with a zinc(II) ion, the agent has been demonstrated to bind to serum albumin. Imaging glucose-stimulated zinc secretion (GSZS) from secretory tissues has proven useful at assessing organ function and health; current probes to detect zinc secretion by MRI have so far been limited to gadolinium-based sensors. Disclosed herein are manganese-based zinc sensors which show that pancreatic and prostatic zinc detection is not compromised when using Mn instead of Gd for imaging GSZS in vivo. Biodistribution studies indicate that the Mn-based sensor is cleared intact after renal filtration but degraded during hepatobiliary clearance. Furthermore, in some embodiments, a lower concentration of the contrast agent which possesses a higher potency can be used to image small biological targets. Finally, in some embodiments, the contrast agent has additional advantages in terms of toxicity and adverse effects associated with the compound class. In some embodiments, compounds of the disclosure also have the advantage that they are more efficacious than, less toxic than, longer acting than, more potent than, produce fewer side effects than, more easily absorbed than, and/or have a better pharmacokinetic profile (e.g., higher oral bioavailability and/or lower clearance) than, and/or have other useful pharmacological, physical, or chemical properties over, known compounds, whether for use in the indications stated herein or otherwise.

A. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means=NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof;

"mercapto" means —SH; and "thio" means=S; "sulfonyl" means —S(O)₂—; and "sulfinyl" means —S(O)—.

In the context of chemical formulas, the symbol "—" means a single bond, "=" means a double bond, and "≡" means triple bond. The symbol "- - - -" represents an optional bond, which if present is either single or double. The symbol "====" represents a single bond or a double bond. Thus, the formula

covers, for example,

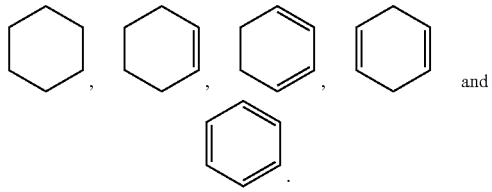

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀■" means a single bond where the group attached to the thick end of the wedge is "out of the page." The symbol "⦀⦀⦀" means a single bond where the group attached to the thick end of the wedge is "into the page". The symbol "∿∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

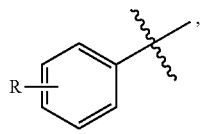

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

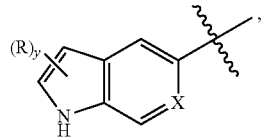

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C≤10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefines" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/ groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

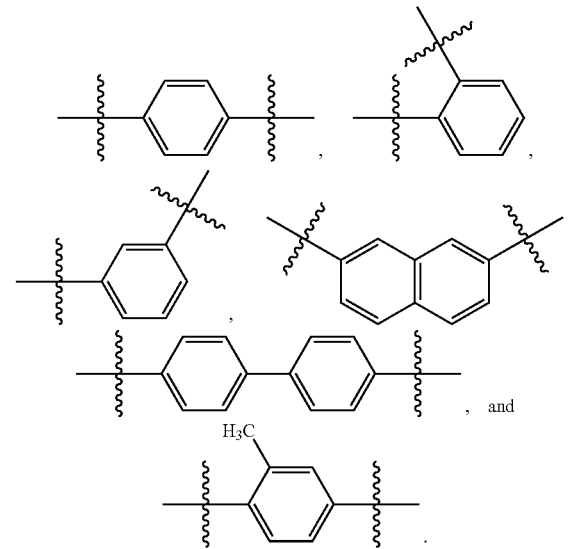

An "arene" refers to the class of compounds having the formula H—R, wherein R is aryl as that term is defined above. Benzene and toluene are non-limiting examples of arenes.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

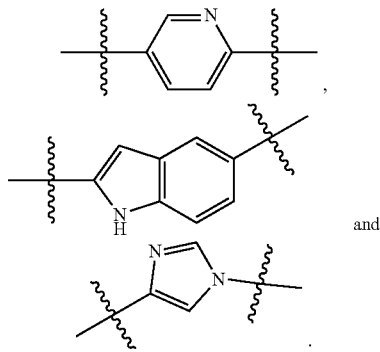

and

When a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. For example, the following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "effective," as that term is used in the specification and/or claims, means adequate to accomplish a desired, expected, or intended result.

The term "metal complex" is a compound comprising at least one compound which can act as a ligand (i.e. contains at least one pair of electrons, a charge, or an empty orbital) and at least one metal ion, wherein the ligand and the metal ion are attached to one another by one or more metal-ligand bonds.

The term "deprotonated form" is a compound in which one or more acidic hydrogen atoms have been removed. In some embodiments, an acidic hydrogen has a $pK_a$ less than 20. In a preferred embodiment, the $pK_a$ is less than 10. In a more preferred embodiment, the $pK_a$ is less than 7.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M- - - -C, and M 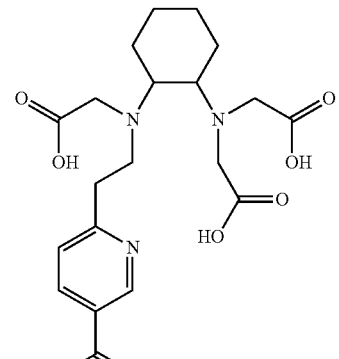 C, each refers to a bond of any and type and order between a metal atom and a carbon atom.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

B. Compounds

The compounds of the present disclosure are shown below in Table 1. These compounds may also be referred to as ligands, complexes, and/or hydrates throughout the application.

TABLE 1

Compounds of the Present Disclosure

| Compound Number | Structure |
|---|---|
| 1 | 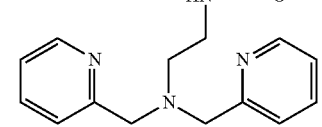 |

TABLE 1-continued

Compounds of the Present Disclosure

| Compound Number | Structure |
|---|---|
| 2 | 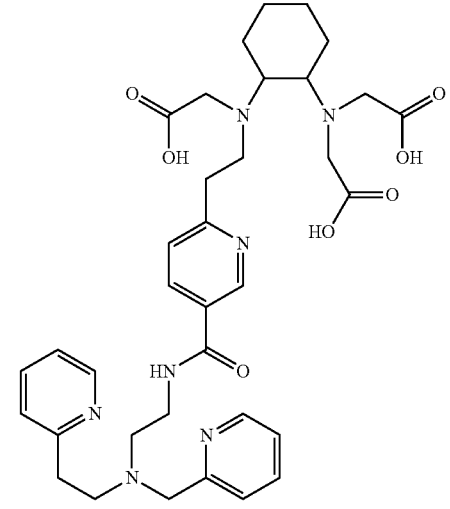 [SMILES: O=C(O)CN(CCc1ccc(C(=O)NCCN(CCc2ccccn2)Cc2ccccn2)cn1)C1CCCCC1N(CC(=O)O)CC(=O)O] |
| 3 | 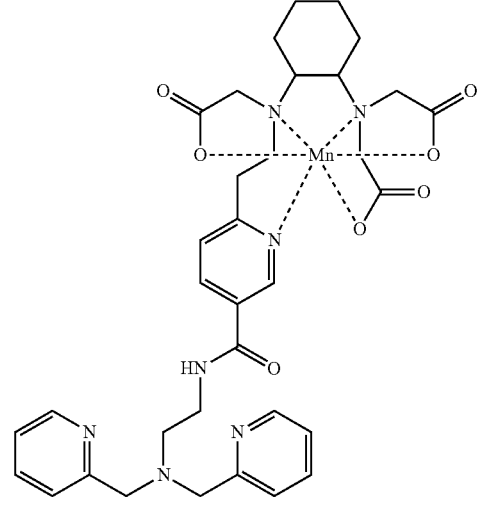 |
| 4 | 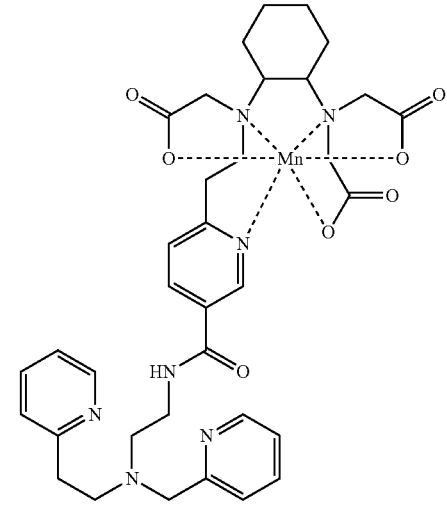 |
| 5 | |
| 6 | |

The compounds of the present disclosure are shown, for example, above, in the summary section and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

Compounds of the present disclosure may contain one or more asymmetrically-substituted carbon or nitrogen atom and may be isolated in optically active or racemic form.

Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration. In some embodiments, the present compounds may contain two or more atoms which have a defined stereochemical orientation.

Chemical formulas used to represent compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

In some embodiments, the compounds of the present disclosure have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

C. Preparation of Ligand and Imaging Characterization

1. Synthesis

The precursor for the ligand was synthesized following previously published protocols (Gale, et al., 2015). Bis(pyridine-2-ylmethyl)ethane-1,2-diamine was coupled to the precursor using PyAOP and DIPEA. The tert-butyl groups were hydrolyzed using acid (HCl or TFA) to obtain the ligand. $MnCl_2$ at pH 6.5 was used to incorporate $Mn^{2+}$.

Furthermore, the complex can be metalated before, during, or after the synthesis of the functional groups on 1,2-diamine ligand provided that the synthetic methods are not negatively affect by the presence of the metal ion. In some embodiments, the metal ion is introduced into the 1,2-diamine compound after the introduction of the functional groups to the ligand.

2. Relaxometric Studies

In some embodiments, MRI contrast agents are typically characterized by a $T_1$ proton relaxivity value. The relaxivity of low molecular weight Mn-ligand complex that has rapid water exchange kinetics may be dominated by the inner-sphere contribution. Without being bound by theory, the Solomon-Bloembergen-Morgan (SBM) theory of relaxivity predicts that inner-sphere contribution to relaxivity may be dependent on several parameters including the number of inner-sphere water molecules (q), the longitudinal relaxation time of the protons of the water molecule(s) in the inner coordination sphere, the residence time of the inner-sphere water molecule(s) and the tumbling rate of the paramagnetic complex in solution (rotational correlation time) (Caravan, et al., 1999).

3. MRI Imaging and Relaxivity Measurements

The efficacy of the probe is measured by the longitudinal relaxation rate of the water protons, which is known as relaxivity ($r_1$) (Shiraishi, et al., 2010; Huang, et al., 2011) or the measurement of other physical parameters. Without being bound by theory, according to the Bloembergen-Solomon-Morgan theory, in some embodiments, the residence lifetime of the coordinated water molecules and the rotational correlation times are factors for enhancing the relaxivities of manganese complexes, which are related to the intrinsic structural parameters. In some embodiments, the relaxation theory also predicts that higher relaxation rates can be obtained upon increase of the rotational correlation time of complexes.

D. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Synthesis and General Methods

Synthesis of Compound 5: The precursor for the ligand was synthesized following previously published protocols (Gale et al., 2015). The synthesis of compounds 1 and 5 are outlined in Scheme 1.

Scheme 1. Synthetic route to access compounds 1 and 5

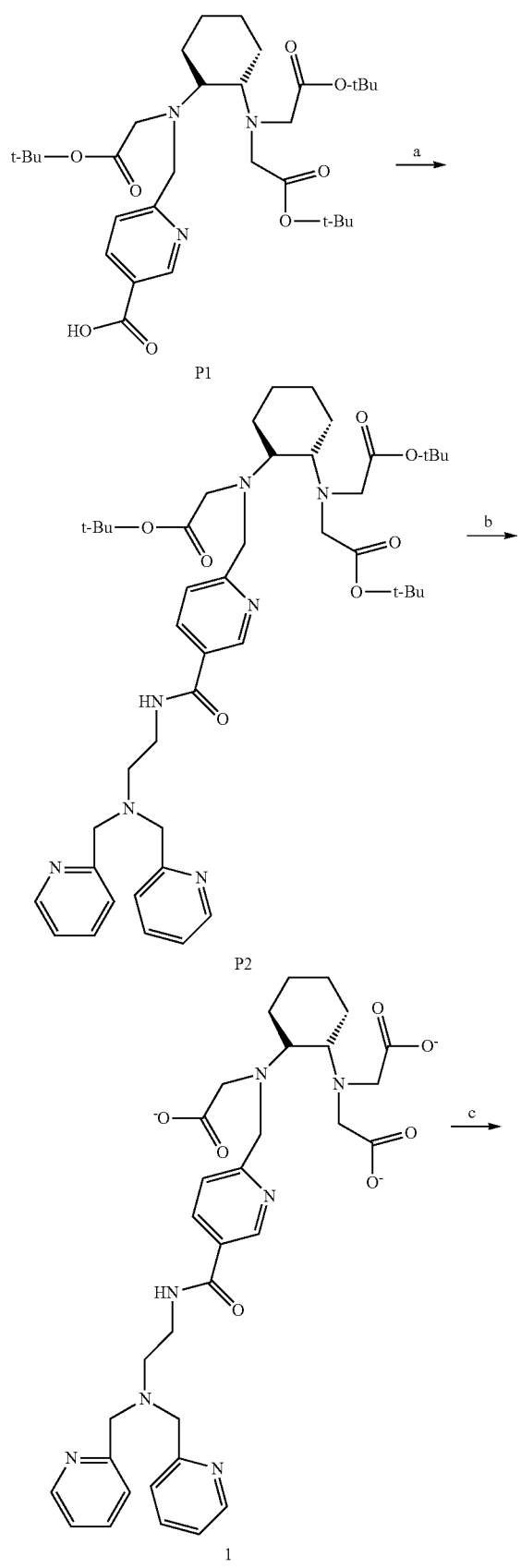

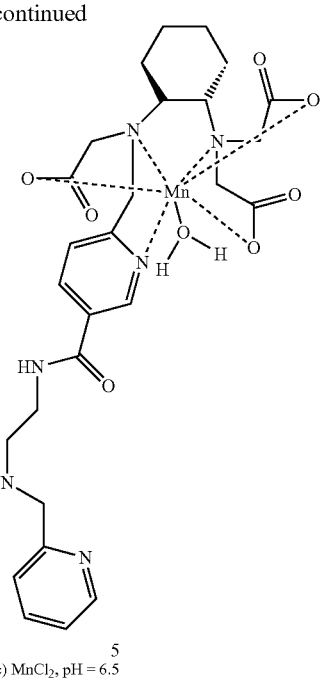

a) PyAOP, DMF, DIPEA; b) 3N HCl; c) MnCl$_2$, pH = 6.5

N-(6-methyl)-(2-(bis(pyridin-2-ylmethyl)amino)ethyl)-nicotinamido-N,N',N'-trans-1,2-cyclohexylenediamine-tri-tertbutylacetate (P2): To a stirred solution of P1 (0.592 g, 1 mmol), (7-azabenzotriazolyl-1-yloxy)trispyrrilodinophosphonium hexaflurophosphate (1.042 g, 2 mmol) and N,N-diisopropylethylamine (1.29 g. 10 mmol) in 5 mL anhydrous N,N-dimethylformamide was added N$^1$, N$^1$,bis(pyridine-2-ylmethyl)ethane-1,2-diamine (0.482 g, 2 mmol). The mixture was stirred at room temperature for 2 hours. 100 ml of dichloromethane was added, washed with water (50 mL×3) followed by brine (100 mL). The organic layer was dried over Na$_2$SO$_4$ and concentrated to a brown oil. The crude product was purified by flash chromatography (Alumina, 5% MeOH in dichloromethane) to yield 0.490 g of P2 as a pale brown oil.

Compound (1): Compound P2 (0.204 g. 0.25 mmol) was stirred in 5 mL 3N HCl for 48 hours. Acid was removed in vacuo and the residue lyophilized to yield compound 1 as an off-white solid in quantitative yield (0.16 g).

Mn—N-(6-methyl)-(2-(bis(pyridin-2-ylmethyl)amino) ethyl)-nicotinamido-N,N' N'-trans-1,2-cyclohexylenediamine-triacetate (5): Compound 1 was dissolved in 5 mL water and pH adjusted to 6.5. MnCl$_2$.4H$_2$O (0.059 g. 0.3 mmol) was added and pH re-adjusted to 6.5. The complex formation was monitored using LC-MS. The mixture was purified on an RP-HPLC C18 column using 50 mM ammonium acetate buffer at pH 6.5 and acetonitrile containing 5% 50 mM ammonium acetate buffer at pH 6.5 as the mobile phase.

Relaxometry: Varying concentrations of 5 (0-1 mM) were incubated with 2 mM ZnCl$_2$, and 0.6 mM human serum albumin (HSA) at 37° C. T$_1$ and T$_2$ measurements were obtained at 1.5 T using a Bruker relaxometer. T$_1$ was obtained by an inversion recovery sequence (IR, first pulse=10 ms, TR=10 s, TI=10-2500 ms), and T$_2$ by a Carr-Prucell-Meiboom-Gill (CPMG, TE/TR=5/10000 ms, NE=700).

In Vivo MRI: Male C57B16 mice were imaged at 4.7 T and 9.4 T using Varian/Agilent scanners. Mice were anesthetized with 2-5% isofluorane/oxygen mixture and their body temperature was maintained at 37° C. using heated airflow. Two ge3d $T_1$-weighted scans were obtained as a baseline (TE/TR=1.69/3.35 ms, Average=4, θ=20°). Mice then received 0.07 mmol/kg 5 i.v. plus 2.2 mmol/kg D-Glucose i.p. and sequential 3d $T_1$-weighted scans were obtained for 90 minutes until clearance of the agent was evident. Images were analyzed using ImageJ, organs of interest were identified, and ROIs were measured and normalized to muscle ROIs within the same slice and time point. The change in MR signal intensity is reported as a percentage compared to pre-injection scans.

Tissue ICP-AES: Biodistribution of 5 was measured in tissues 15 and 90 min after injection of (1) 0.07 mmol/kg 5 plus 2.2 mmol/kg D-glucose, (2) 0.07 mmol/kg 5 plus saline, and (3) 0.035 mmol/kg $MnCl$ plus 2.2 mmol/kg D-glucose into male $C_{57}B16$ mice. The tissue weights were recorded and digested in aqua regia for 24 hours, the digested tissue was heated to 120° C. until evaporated and re-suspended in 0.5 M HCl. For ICP-AES, Mn, Fe, and Zn concentrations were obtained by comparing to a known metal standard.

Example 2: Results and Discussion

Figures 2A, 2B:
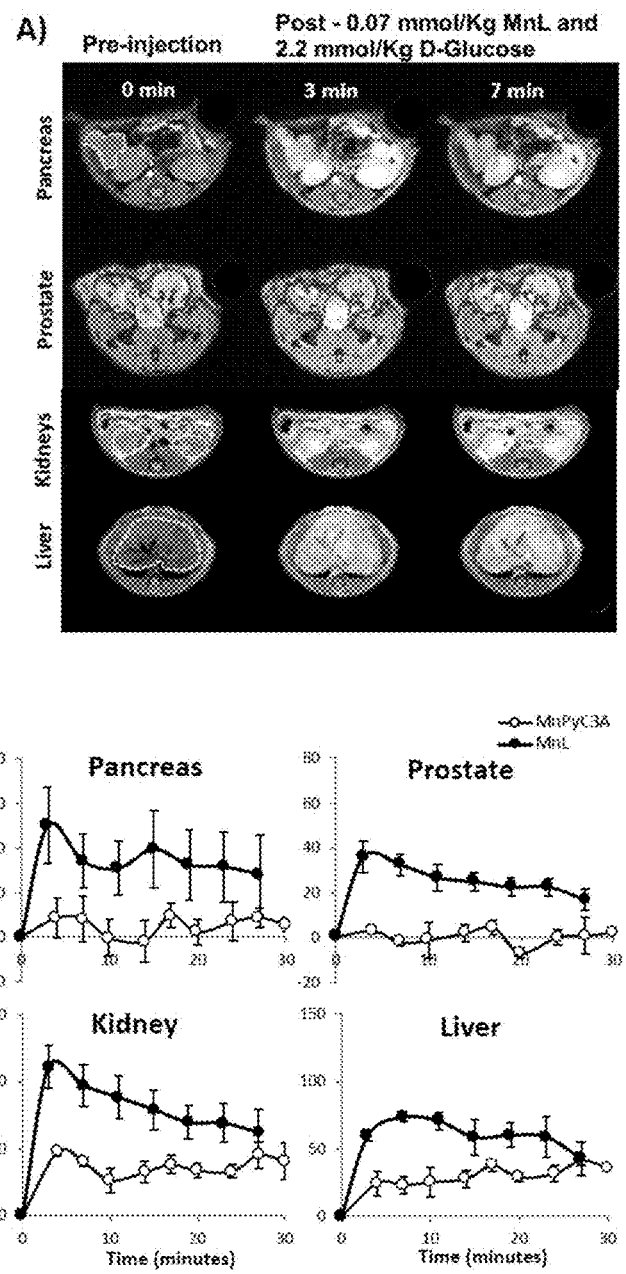
FIGS. 2A & 2B show in vivo evaluation of 5 as a zinc sensor by 3D T$_1$W-MRI before and after injection of 5 0.07 mmol/kg i.v. and D-glucose 2.2 mmol/kg i.p. $B_0$=9.4 T (FIG. 2A); and MRI signal intensity change measured from ROIs placed on each organ, normalized to a muscle ROI and calculated as a percentage change compared to pre-injection scans. $B_0$=4.7 T, N=4 (FIG. 2B).
Figures 3A, 3B:
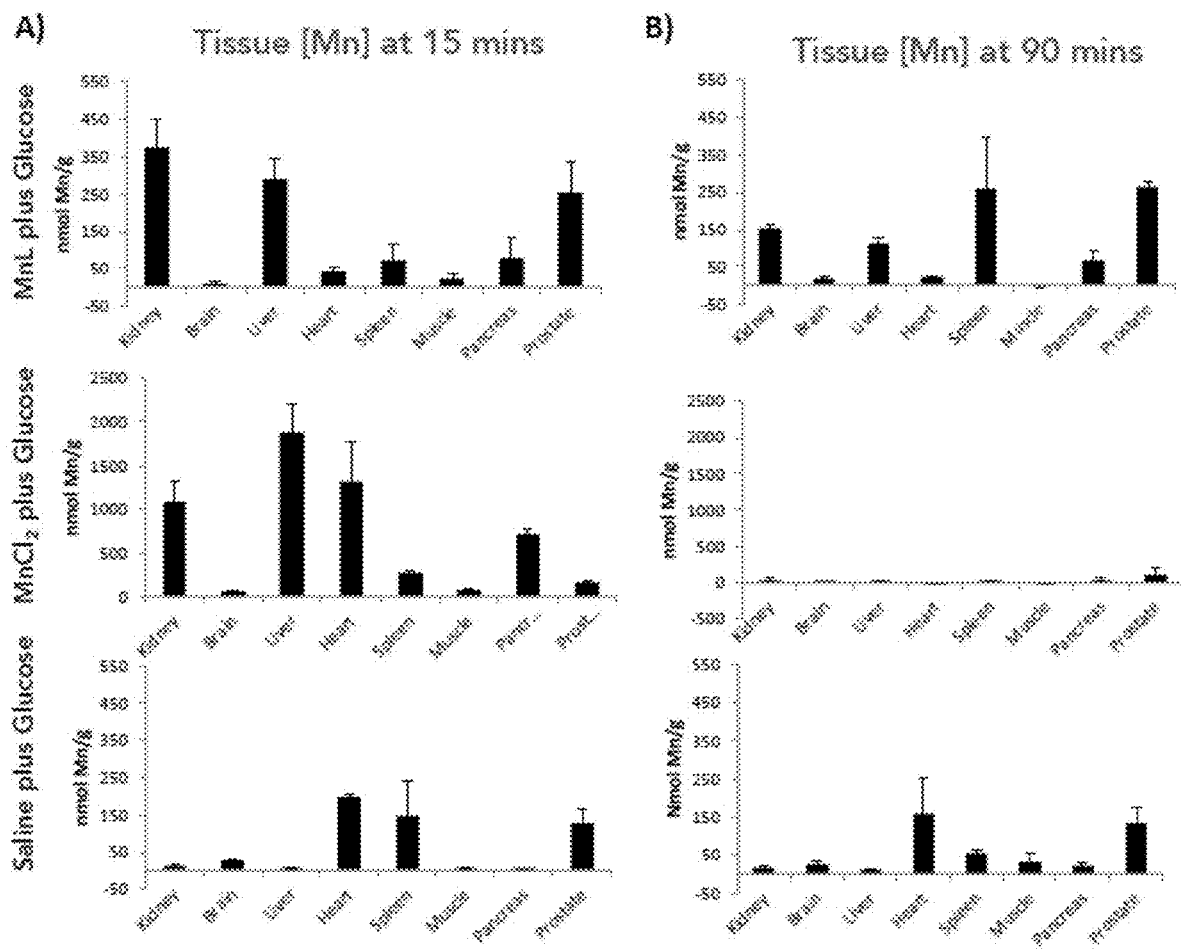
FIGS. 3A & 3B show manganese content in tissues as measured by ICP-AES 15 or 90 minutes after injection of 0.07 mmol/kg 5 (i.v.) plus 2.2 mmol/kg D-glucose (i.p.), N=3 each (FIG. 3A), or 0.035 mmol/kg MnCl (i.v.) plus 2.2 mmol/kg D-glucose (i.p.), N=3 each (FIG. 3B).

Zinc sensor 5 shows strong zinc binding capabilities ($K_{D(Zn)}$=90 nM), relaxometry showed that 5 has a $r_1/r_2$=3.5/6.0 $mM^{-1}s^{-1}$ and that upon binding to $Zn^{2+}$ and HSA, $r_1/r_2$=14.1/22.4 $mM^{-1}s^{-1}$ (see FIG. 1). The in vivo images show that 5 is readily detected in $T_1$-weighted images. Enhancement in the pancreas, prostate, kidneys, and liver at 4 minutes post injection is illustrated in FIG. 2A. The normalized signal change from each organ and washout after 90 minutes is shown in FIG. 2B. 5 is excreted as an intact complex after renal filtration (as observed by LC-MS of urine) but degraded during hepatobiliary clearance (as observed by LC-MS of bile). Control experiments showed marginal enhancement in the prostate and pancreas when D-glucose was not co-injected suggesting that 5 is uniquely sensitive to zinc. Tissue measurements of Mn content by ICP-AES show the clearance path and biodistribution. After 15 minutes post-injection, 5 (presumably the chelated form) is found primarily in the kidneys, liver, pancreas, and prostate, as shown in FIG. 3A. After 90 minutes, the Mn content was greatly diminished in kidney and liver tissues but accumulated in the spleen and in the prostate. The later observation may reflect Mn in the prostatic urethra during excretion of the agent. The tissue biodistribution of Mn after injection of $MnCl_2$ i.v. is summarized in FIG. 3B and show that $MnCl_2$ is excreted renally and more overwhelmingly via the hepatobiliary system. Accumulation in the heart is indicative of unchelated Mn as observed in the mice injected with $MnCl_2$ (Gale et al., 2015), while the distribution of 5 shows no accumulation in the heart indicating that 5 remains intact during circulation.

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

PCT Application WO 2002/043775
US Patent Application US 2011/0009605
Caravan, et al., *Chemical Reviews*, 99:2293-2352, 1999.
Caravan, *Chemical Society Reviews*, 35:512-523, 2006.
Esqueda, et al., *J. Am. Chem. Soc.*, 131:11387-11391, 2009.
Gale, et al., *J. Am. Chem. Soc.*, 137:15548-15557, 2015.
*Handbook of Pharmaceutical Salts: Properties, and Use*, Stahl and Wermuth Eds.), Verlag Helvetica Chimica Acta, 2002.
Hirayama, et al., *Chem. Commun.*, 22:3196-3198, 2009
Huang, et al., *Biomaterials*, 32:5177-5186, 2011.
Kiyose, et al., *J. Am. Chem. Soc.* 128:6548-6549, 2006.
*March's Advanced Organic Chemistry: Reactions, Mechanisms, and Structure*, 2007.
Rohrer, et al., *Investigative Radiology*, 40:715-724, 2005.
Shiraishi, et al., *Journal of Controlled Release*, 148:160-167, 2010.
Weissleder, *Science*, 312:1168-1171, 2006.
Woods and Sherry, *Inorg. Chem.*, 42:4401-4408, 2003.
Yu, et al., *J. Am. Chem. Soc.*, 137:14173-14179, 2015.

What is claimed is:

1. A compound of the formula:

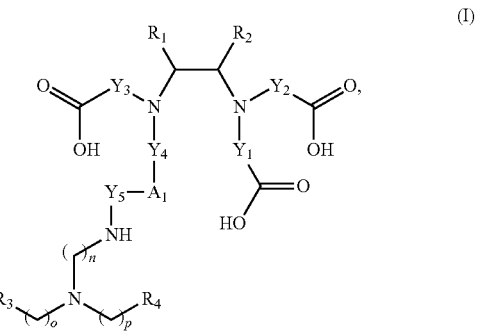

wherein:
n is 1, 2, 3, 4, 5, or 6;
o and p are each independently 1, 2, or 3;
$A_1$ is heteroarenediyl$_{(C≤12)}$ or substituted heteroarenediyl$_{(C≤12)}$;
$R_1$ and $R_2$ are each independently hydrogen; or
alkyl$_{(C≤12)}$, aryl$_{(C≤12)}$, heteroaryl$_{(C≤12)}$, or a substituted version of any of these groups; or
$R_1$ and $R_2$ are taken together and are alkanediyl$_{(C≤12)}$, substituted alkanediyl$_{(C≤12)}$, alkenediyl$_{(C≤12)}$, or substituted alkenediyl$_{(C≤12)}$;
$R_3$ and $R_4$ are each independently heteroaryl$_{(C≤12)}$ or substituted heteroaryl$_{(C≤12)}$;
$Y_1$, $Y_2$, $Y_3$, and $Y_4$ are each independently alkanediyl$_{(C≤4)}$ or substituted alkanediyl$_{(C≤4)}$; and
$Y_5$ is a covalent bond or —C(O)—; or
alkanediyl$_{(C≤12)}$, substituted alkanediyl$_{(C≤12)}$, -alkanediyl$_{(C≤12)}$-C(O)—, or substituted -alkanediyl$_{(C≤12)}$-C(O)—;

or a metal complex, a deprotonated form, a hydrate, or a salt thereof.

2. The compound of claim 1, further defined as:

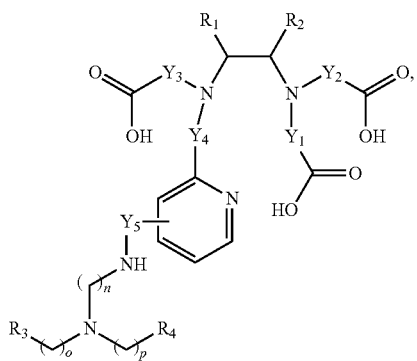

(II)

wherein:
n is 1, 2, 3, 4, 5, or 6;
o and p are each independently 1, 2, or 3;
$R_1$ and $R_2$ are each independently hydrogen; or
alkyl$_{(C\le12)}$, aryl$_{(C\le12)}$, heteroaryl$_{(C\le12)}$, or a substituted version of any of these groups; or
$R_1$ and $R_2$ are taken together and are alkanediyl$_{(C\le12)}$, substituted alkanediyl$_{(C\le12)}$, alkenediyl$_{(C\le12)}$, or substituted alkenediyl$_{(C\le12)}$;
$R_3$ and $R_4$ are each independently heteroaryl$_{(C\le12)}$ or substituted heteroaryl$_{(C\le12)}$;
$Y_1$, $Y_2$, $Y_3$, and $Y_4$ are each independently alkanediyl$_{(C\le4)}$ or substituted alkanediyl$_{(C\le4)}$; and
$Y_5$ is a covalent bond or —C(O)—; or
alkanediyl$_{(C\le12)}$, substituted alkanediyl$_{(C\le12)}$, -alkanediyl$_{(C\le12)}$-C(O)—, or substituted -alkanediyl$_{(C\le12)}$-C(O)—;
or a metal complex, a deprotonated form, a hydrate, or a salt thereof.

3. The compound of either claim 1, further defined as:

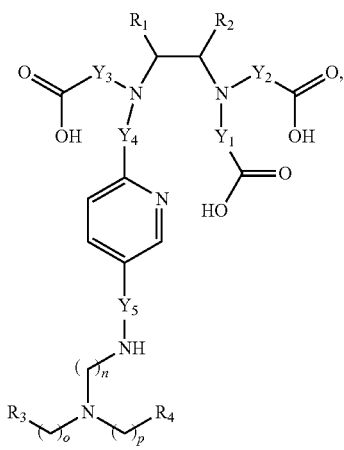

(III)

wherein:
n is 1, 2, 3, 4, 5, or 6;
o and p are each independently 1, 2, or 3;
$R_1$ and $R_2$ are each independently hydrogen; or
alkyl$_{(C\le12)}$, aryl$_{(C\le12)}$, heteroaryl$_{(C\le12)}$, or a substituted version of any of these groups; or
$R_1$ and $R_2$ are taken together and are alkanediyl$_{(C\le12)}$, substituted alkanediyl$_{(C\le12)}$, alkenediyl$_{(C\le12)}$, or substituted alkenediyl$_{(C\le12)}$;
$R_3$ and $R_4$ are each independently heteroaryl$_{(C\le12)}$ or substituted heteroaryl$_{(C\le12)}$;
$Y_1$, $Y_2$, $Y_3$, and $Y_4$ are each independently alkanediyl$_{(C\le4)}$ or substituted alkanediyl$_{(C\le4)}$; and
$Y_5$ is a covalent bond or —C(O)—; or
alkanediyl$_{(C\le12)}$, substituted alkanediyl$_{(C\le12)}$, -alkanediyl$_{(C\le12)}$-C(O)—, or substituted -alkanediyl$_{(C\le12)}$-C(O)—;
or a metal complex, a deprotonated form, a hydrate, or a salt thereof.

4. The compound of according to claim 1, further defined as:

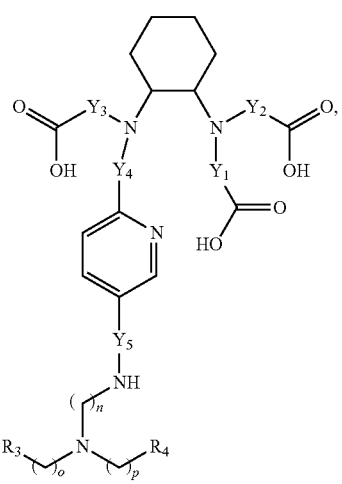

(IV)

wherein:
n is 1, 2, 3, 4, 5, or 6;
o and p are each independently 1, 2, or 3;
$R_3$ and $R_4$ are each independently heteroaryl$_{(C\le12)}$ or substituted heteroaryl$_{(C\le12)}$;
$Y_1$, $Y_2$, $Y_3$, and $Y_4$ are each independently alkanediyl$_{(C\le4)}$ or substituted alkanediyl$_{(C\le4)}$; and
$Y_5$ is a covalent bond or —C(O)—; or
alkanediyl$_{(C\le12)}$, substituted alkanediyl$_{(C\le12)}$, -alkanediyl$_{(C\le12)}$-C(O)—, or substituted -alkanediyl$_{(C\le12)}$-C(O)—;
or a metal complex, a deprotonated form, a hydrate, or a salt thereof.

5. The compound of according to claim 1, further defined as:

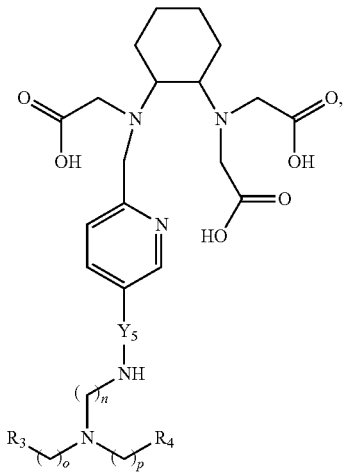

(V)

wherein:
n is 1, 2, 3, 4, 5, or 6;
o and p are each independently 1, 2, or 3;
$R_3$ and $R_4$ are each independently heteroaryl$_{(C \leq 12)}$ or substituted heteroaryl$_{(C \leq 12)}$;
$Y_5$ is a covalent bond or —C(O)—; or alkanediyl$_{(C \leq 12)}$, substituted alkanediyl$_{(C \leq 12)}$, -alkanediyl$_{(C \leq 12)}$-C(O)—, or substituted -alkanediyl$_{(C \leq 12)}$-C(O)—;

or a metal complex, a deprotonated form, a hydrate, or a salt thereof.

6. The compound according to claim 1, wherein $R_3$ is heteroaryl$_{(C \leq 12)}$.

7. The compound according to claim 1, wherein p is 1 or 2.

8. The compound according to claim 1, wherein $Y_5$ is —C(O)—.

9. The compound of claim 1 further defined as:

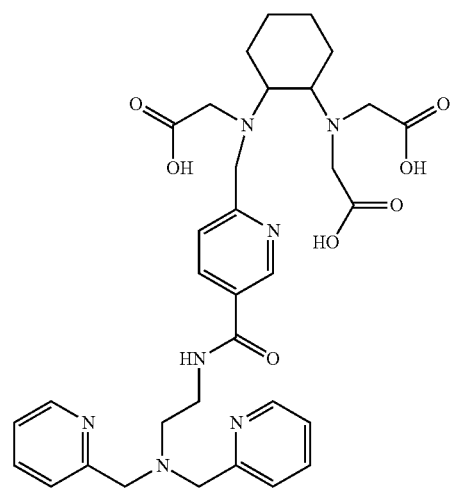

or

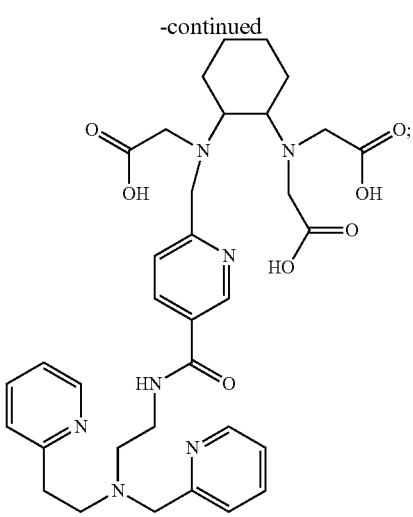

or a metal complex, a deprotonated form, a hydrate, or a salt thereof.

10. The compound of claim 1, further defined as a metal complex of the formula:

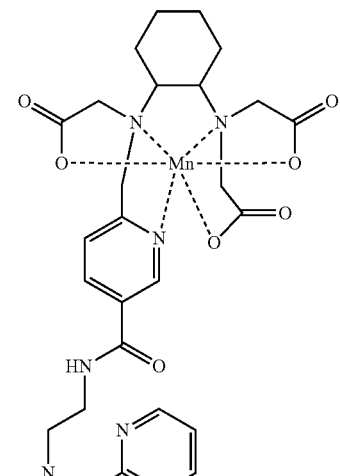

or

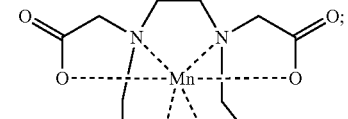

or a deprotonated form, a hydrate, or a salt thereof.

11. The compound of claim 1, further defined as a hydrate of the formula:

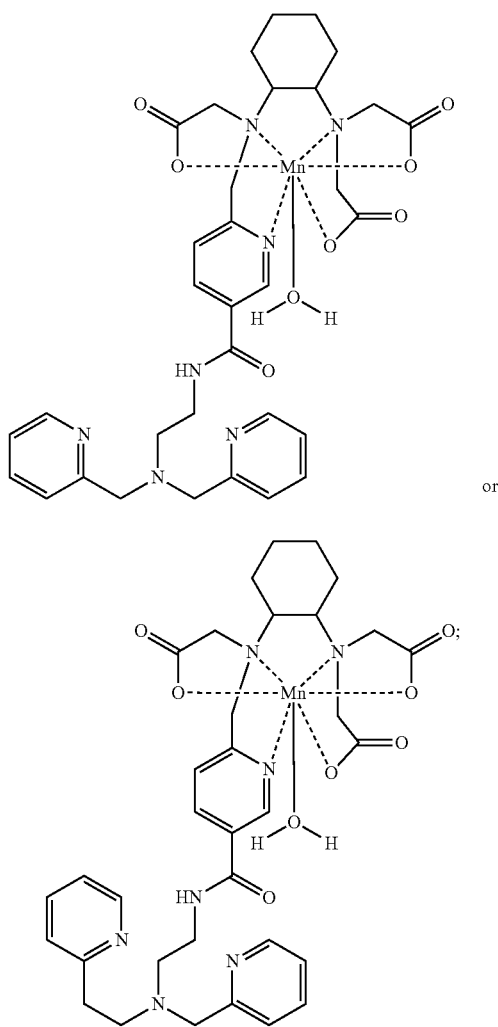

or a deprotonated form or a salt thereof.

12. A pharmaceutical composition comprising a compound of claim 1 and a pharmaceutically acceptable carrier.

13. The pharmaceutical composition of claim 12, wherein the composition is formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion.

14. The pharmaceutical composition of claim 13, wherein the composition is formulated for administration intraprostatically or intravenously.

15. The pharmaceutical composition according to claim 12, formulated as a unit dose form in an amount sufficient to image a patient when administered thereto.

16. A method of imaging a patient comprising the steps of:
  a) administering to the patient a compound or composition of claim 1; and
  b) obtaining an imaging scan of the patient.

17. A method of imaging the pancreas in vivo in a patient to determine the onset of β-cell degeneration comprising the steps of:
  a) administering to the patient a compound or composition of claim 1;
  b) obtaining an imaging scan of the patient; and
  c) determining the presence of $Zn^{2+}$ ions.

18. A method of imaging the prostate in vivo in a patient to determine the presence of a prostate tumor comprising the steps of:
  a) administering to the patient a compound or composition of claim 1;
  b) obtaining an imaging scan of the patient; and
  c) determining the presence of $Zn^{2+}$ ions.

* * * * *